United States Patent [19]

Chibnik

[11] 4,219,431
[45] Aug. 26, 1980

[54] AROYL DERIVATIVES OF ALKENYLSUCCINIC ANHYDRIDE AS LUBRICANT AND FUEL ADDITIVES

[75] Inventor: Sheldon Chibnik, Cherry Hill, N.J.

[73] Assignee: Mobil Oil Corporation, New York, N.Y.

[21] Appl. No.: 709,489

[22] Filed: Jul. 28, 1976

Related U.S. Application Data

[63] Continuation-in-part of Ser. No. 542,474, Jan. 20, 1975, abandoned.

[51] Int. Cl.$^2$ .......................... C10L 1/18; C10L 1/22; C10M 1/26; C10M 1/36
[52] U.S. Cl. ...................................... 252/33.4; 44/63; 44/68; 252/33; 252/49.7; 252/51.5 A; 252/56 R; 252/56 D
[58] Field of Search ............ 252/51.5 A, 56 R, 479 S, 252/33, 33.4, 49.7, 56 D; 44/63, 68

[56] References Cited

U.S. PATENT DOCUMENTS

| | | | |
|---|---|---|---|
| 2,345,006 | 3/1944 | Ross et al. | 260/479 S X |
| 3,032,502 | 5/1962 | Barnes et al. | 252/56 D X |
| 3,381,022 | 4/1968 | Le Suer | 260/479 S X |
| 3,442,808 | 5/1969 | Traise et al. | 252/51.5 A X |
| 3,493,520 | 2/1970 | Verdol et al. | 252/51.5 A |
| 3,542,680 | 11/1970 | Le Suer | 252/56 R X |
| 3,632,510 | 1/1972 | Le Suer | 252/51.5 A X |
| 3,779,928 | 12/1973 | Schlicht | 252/32.5 X |
| 3,910,845 | 10/1975 | Coon | 252/56 D X |
| 3,936,472 | 2/1976 | Kinney et al. | 252/56 D X |
| 4,011,167 | 3/1977 | Chibnik et al. | 252/49.7 X |
| 4,097,389 | 6/1978 | Andress | 44/63 X |
| 4,098,585 | 7/1978 | Vartanian et al. | 44/63 |

FOREIGN PATENT DOCUMENTS

825212 10/1969 Canada ............................... 252/51.5 A

*Primary Examiner*—Thomas A. Waltz
*Attorney, Agent, or Firm*—Charles A. Huggett; Raymond W. Barclay; Claude E. Setliff

[57] ABSTRACT

Lubricant compositions containing a lubricant and a minor amount of a derivative of alkenylsuccinic anhydride are provided. Such derivatives include the reaction product of (1) the product of reaction between an alkenylsuccinic acid, ester or anhydride and a hydroxyaromatic compound; (2) the product of reaction between (1) and an amine selected from the group consisting of an alkanepolyol such as an amino alkanediol and a polyalkylene polyamine; (3) the reaction product of (2) and an aldehyde; (4) the reaction product of (3) with a metal salt capable of forming a stable complex with amines; (5) the reaction product of (2) with a metal salt; and (6) the product of reaction between an alkenylsuccinic acid or anhydride and an alkyl phenyl ether.

43 Claims, No Drawings

AROYL DERIVATIVES OF ALKENYLSUCCINIC ANHYDRIDE AS LUBRICANT AND FUEL ADDITIVES

CROSS REFERENCE TO RELATED APPLICATIONS

This is a continuation-in-part of application Ser. No. 542,474, filed Jan. 20, 1975, now abandoned.

BACKGROUND OF THE INVENTION

1. Field of the Invention

The invention is concerned with stabilized fuels and lubricants. More particularly, it relates to fuel and lubricant compositions to which have been added an aroyl derivative of an alkenylsuccinic anhydride.

2. Discussion of the Prior Art

A great deal of efforts is being directed to providing a lubricant which will permit present-day automotive engines to be operated at a high level of efficiency over long periods of time. A difficulty arises because lubricating oils tend to deteriorate under the conditions of use, with attendant formation of sludge, lacquer and resinous materials which adhere to the engines parts, thereby lowering the operating efficiency of the engine. To counteract the formation of these deposits, certain chemical additives have been found which, when added to lubricating oils, have the ability to keep the deposit-forming materials suspended in the oil, so that the engine is kept clean and in efficient operating condition for extended periods of time. These added agents are known in the art as detergents or dispersants.

Metallo-organic compounds are particularly useful as additives in this respect. However, the troublesome deposits which form on the skirt of the piston and on the walls of the combustion chamber, as well as on valves and spark plugs are also partially attributable to these metal containing additives employed in the lubricant. Whenever oil is burned in the engine, as occurs with the oil film present on the cylinder wall during the combustion stroke, many metal containing additives present in the oil may form an ash which is partially deposited on the various surfaces of the combustion chamber and on those of the spark plugs and valves.

Several known non-metallic detergents have previously been used in lubricating compounds. However, they have not proved to be entirely satisfactory. Additives which are particularly effective are based upon condensation products of a hydroxyaromatic compound, an aldehyde and an amine, the so-called Mannich reaction. These additives are multi-functional improvers especially adapted for mineral oils and as pour point depressants therein. These compounds have also been recognized as exhibiting detergent properties. A preference has existed for the use of hydroxyaromatics which are unsubstituted, particularly phenol and alpha and beta naphthols.

U.S. Pat. No. 3,808,131 discloses a metal coordinated complex, useful as a detergent in lube oils and fuels, made by reacting an amine-acid product with an alkenylsuccinic anhydride or acid and a metal salt. Further, U.S. Pat. No. 3,755,167 describes a lube or fuel additive prepared by reacting an amine-aldehyde product with an alkenylsuccinic acid or anhydride and a metal salt. This additive is also useful as a detergent.

Other patents include U.S. Pat. Nos. 3,215,728, 3,493,520, 3,522,179, 3,558,743 and 3,632,510.

U.S. Pat. No. 3,215,728 discloses the reaction between an alkylphenol and a diester of maleic acid. The phenol is attached directly to the maleate double bond, and there is no carbon chain on the molecule of 50 carbon atoms or more.

U.S. Pat. Nos. 3,493,520 and 3,558,743 relate to products made from succinic acid, amine, phenol and aldehyde. However, there is no disclosure in this patent of the necessity for having a $C_{50}$ alkenyl on the succinic compound. In addition, it is evident that the products are in no way similar to those of the present invention since the phenol is not attached to the carbon system of the succinic compound, but to the imide formed during reaction (see Columns 5 and 6 of 3,493,520).

U.S. Pat. Nos. 3,522,179 and 3,632,510 disclose products made by reacting a hydrocarbon-substituted succinic anhydride with, for example, phenol, and salts thereof. It is obvious, however, that the products are different. In Column 5 of U.S. Pat. No. 3,522,179 and Column 6 of U.S. Pat. No. 3,632,510, it is shown that the hydroxyl compound reacts directly with the anhydride function to form the ester. This is precisely the reaction applicant wishes to avoid.

SUMMARY OF THE INVENTION

The invention provides lubricant and fuel compositions comprising a major amount of a liquid hydrocarbon fuel or a lubricating oil and a detergent amount of a product selected from the group consisting of: (1) the product of reaction between an alkenylsuccinic acid, ester or anhydride and a hydroxyaromatic compounds; (2) the product of reaction between (1) and an amine selected from the group consisting of an alkanepolyol such as an amino alkanediol and a polyalkylene polyamine; (3) the reaction product of (2) and an aldehyde; (4) the reaction product of (3) with a metal salt capable of forming a stable complex with amines; (5) the reaction product of (2) with a metal salt; and (6) the product of reaction between an alkenylsuccinic acid or anhydride and an alkyl phenyl ether.

DESCRIPTION OF SPECIFIC EMBODIMENTS

(1) The reaction of alkenylsuccinic acid, ester or anhydride with a hydroxyaromatic compound In general, these alkenylsuccinic compounds undergo reaction with a hydroxyaromatic compound, for example, phenol, under relatively mild conditions. The preferred temperatures are from about 20° C. to about 150° C. Broadly, however, the temperatures can range from about −20° C. to about 225° C., depending upon the time of reaction and the size of the substituent on the hydroxyaromatic compound.

The alkenylsuccinic compound is one wherein the alkenyl group is a hydrocarbon containing a double bond and containing from 25 to about 300 carbon atoms, preferably from 50 to 100 carbon atoms. These are produced by known techniques from an olefin or polyolefin and maleic anhydride. The olefin may be a simple alkene, such as 1-octene, 1-decene, 1-dodecene, and so forth, or it may be a polymer or copolymer of such olefins as ethene, propene, 1-butene, isobutene, 1-hexene, 1-octene and so forth.

The alkenylsuccinic esters include the mono and diesters and may be represented by the formula:

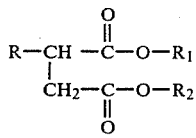

wherein R is the alkenyl group defined hereinabove and $R_1$ and $R_2$ are hydrogen or a hydrocarbyl group having from 1 to 22 carbon atoms. Preferably the group is an alkyl having 1 to 18 carbon atoms. For example, $R_1$ and $R_2$ may be methyl, ethyl, butyl, octyl, dodecyl, octadecyl, eicosyl, and the like. They may also be hydrogen. While both $R_1$ and $R_2$ may be a hydrocarbyl group, either the same or different, only one of them may be hydrogen. In other words, at least one of $R_1$ and $R_2$ must be a hydrocarbyl group.

The term "hydroxyaromatic compound" is meant to include phenol, naphthol, anthrol, hydroquinone, catechol, resorcinol and the like, as well as the high molecular weight members thereof. Representative high molecular weight alkyl-substituted hydroxyaromatic compounds contemplated include polypropenyl-, polybutenyl- and polyamylenephenol and similarly substituted phenols. In addition to the substituted phenol, high molecular weight alkyl-substituted compounds of resorcinol, hydroquinone, catechol, cresol, xylenol, amyl phenol, hydroxydiphenyl, benzylphenol, phenylethylphenol, methylhydroxydiphenyl, alpha and beta naphthol, alpha and beta methylnaphthol, tolylnaphthol, xylynaphthol, benzylnaphthol, anthrol, phenylmethylnaphthol, phenanthrol, chlorophenol, and the like may be used.

It is in general contemplated that the alkyl group will have from 1 to 300 carbon atoms. Preferably, the alkyl will contain from 1 to 50 carbon atoms. The alkyl group may derive from a simple alkene or from a polymer or copolymer of such alkenes. The alkene may be selected from 1-octene, 1-decene, 1-dodecene and the like. The polymers or copolymers may be made from these or from other olefins such as ethene, propene, butene, isobutene and the like.

The polyalkyl hydroxyaromatic compounds useful in this invention may be made by reacting 0.1 to 10 moles of a phenol with 1 mole of an alkylene or a polyalkylene in the presence of an alkylating catalyst, such as $BF_3$ complexes (including the etherate, phenolate or phosphonate complexes), $BF_3$ or HCl gas, $AlCl_3$ and the like, at 0° C. to 250° C. This process is particularly effective when conducted by reacting 1 to 1.5, or especially 1.25 mole, of phenol to 1 mole of a polyalkylene compound in the presence of a $BF_3$ phenolate at about 150° C. The product is conveniently dissolved in an aromatic solvent and then washed with water to remove unreacted components. Upon filtration and removal of the aromatic solvent by distillation, the product, a clear, viscous oil, remains.

The reaction between the alkenylsuccinic compounds and the hydroxyaromatic compound may be advantageously carried out in a reaction system containing about 0.1 to about 10 mole of hydroxyaromatic compound, preferably from about 0.5 to about 2.0 moles, per mole of alkenylsuccinic compound. The time required to complete the reaction is not critical and will range from about 2 hours at the lower temperatures to as little as about 5 minutes when run at the higher temperatures.

This reaction is preferably run in the presence of a solvent. The particular solvent can be selected from a wide variety of materials. In selecting the solvent, one must be used that has a boiling point that will allow easy removal from the final product. Furthermore, the solvent must not react with raw materials or the product. Some of the solvents that may be used in the reaction of an alkenylsuccinic compound with a hydroxyaromatic compound are benzene, toluene, hexane and other aliphatic hydrocarbons and mixtures thereof. Also, some mineral oils and the like can be used.

It is essential in the reaction between the alkenylsuccinic compound and the hydroxyaromatic compound, both as defined herein, that a catalyst be present which directs addition of the phenol to the alkenyl portion of the alkenylsuccinic compound. The preferred catalyst is $BF_3$. Preferably, the hydroxyaromatic compound is used as a complex with the $BF_3$. For instance, reaction of polybutenylsuccinic anhydride with phenol involves reacting the phenol in the form of a phenol-$BF_3$ complex, the complex being made by simple addition, using a solvent, such as benzene, if desired. While the relative proportions are not critical, the complex will preferably contain from about 1 to about 2 moles of phenol per mole of $BF_3$.

An additional advantage of the preferred $BF_3$ is that a stoichiometric amount is not tied up or destroyed by the anhydride group, and the catalyst can be recovered and reused. Furthermore, while the complex used may be preformed, it can also be made in situ during reaction of the succinic compound with the hydroxyaromatic compound by bubbling in $BF_3$ gas during the course of the reaction. The in situ formation is less desirable, however, because of the danger of anhydride rupture by the hydroxyl function.

As is evident from the disclosure thus far, the product of the succinic compound-hydroxyaromatic compound reaction under the conditions of this invention is of uncertain structure. While I do not wish to be bound by speculation as to what the actual structure of the additive is, it is believed that the phenol adds to the double bond of the alkenyl portion of the succinic compound in an alkylation reaction, as illustrated by the following:

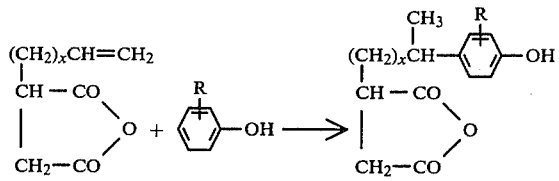

The necessity for having the double bond in the alkenyl portion is evident. Not so evident is the fact that such alkenyl must also contain at least 50 carbon atoms if the alkenylsuccinic compound-hydroxyaromatic compound, and the other compounds of this invention prepared as disclosed herein, are to have effective detergent activity.

(2) The reaction of (1) with an amine

In general aspect, this reaction can be carried out at from about 50° C. to about 250° C., preferably at from about 135° C. to about 200° C. The reaction time is not a critical factor, and it will be governed by the size of the reactants and the temperature selected for reaction.

The amine reactant may be an amino alkanepolyol such as an amino alkanediol wherein the alkane portion may contain from 4 to 10 carbon atoms. One or more of the carbon atoms can be hydroxy-substituted, there being from 2 to 4 such groups. An example of such alkanediol is 2-amino-2-(hydroxymethyl)-1,3-propanediol. The amine may also be a polyalkanepolyamine of the structure $H_2N(RNH)_xH$ wherein R is a 2-5 carbon alkylene group and x is from 1 to 10. The formula includes triethylenetetramine, tetraethylenepentamine, di(methylethylene)triamine, hexapropyleneheptamine and the like.

The amine may be present to the extent of from about 0.1 to about 3.0 moles per mole of the reaction product of (1). As is with the case of reaction (1), a solvent may be used if desired. The useful solvents include benzene, high boiling petroleum oil and the like.

The length of time the reaction is run is not critical. It will, as usual, depend, inter alia, upon the temperature being used and the nature of the reactants. One skilled in the art will be able quite readily to determine when the reaction is complete, as by cessation of amine diminution or by its disappearance.

(3) The reaction of (2) with aldehyde

This reaction can very advantageously be carried out at from about 30° C. to about 200° C., preferably from about 60° C. to about 180° C. The already mentioned solvents may be used. The reaction will be continued until there is no more reaction of aldehyde.

The usable aldehydes preferably include formaldehyde and paraformaldehyde, and will be used to the extent of from about 0.1 to about 5.0 moles of aldehyde per mole of (2).

(4) The reaction of (3) with the preferred salt, zinc methanesulfonate

The zinc methanesulfonate used to illustrate this invention may be prepared by reacting zinc oxide with an aqueous solution of methanesulfonic acid. The reaction with product (3) may be carried out at from about 50° C. to about 225° C., preferably from about 75° C. to about 160° C., in a solvent if desired, for a time sufficient for completion of the reaction with the salt.

In general, the complexing reaction with other metal salts, such as the metal salts of other organosulfonic acids containing a hydrocarbyl group of from 1 to 50 carbon atoms, and metal salts containing the nitrate or sulfate ion, will be run under similar conditions as stated for zinc methane sulfonate. Such salts include those in which the metal therein is chosen from Groups IB, IIB, VB, VIIB, VIII, tin and zirconium. The anion may vary so long as the final complex from such salt is soluble in the medium being used.

The complexing reaction will require at least 0.1 mole of the salt per mole of (3). It will be understood that this is the minimum amount that should be used, and the amount of salt may be as high as 3.0 moles thereof per mole of (3).

(5) The reaction of (1) with a polyalkylenepolyamine and the preferred salt, zinc methanesulfonate Broadly, the reaction of zinc methanesulfonate and the amine, and its reaction with product (1), can be carried out within the temperature ranges set forth in the paragraphs immediately above. Other metal salts are usable in the same way.

The reaction may be carried out by reacting product (1) with the polyalkylamine as outlined under (2) above, using the same conditions, and reacting this product with the various salts mentioned under (3) above, and under the same conditions. However, it is contemplated that the product can be made in other ways. For example, one mole of a polyalkylenepolyamine, as defined hereinabove, from about 0.1 to about 3.0 moles of salt, preferably from about 0.9 to about 2.0 moles, can be reacted, in a mutual solvent, at a temperature of from about 50° C. to about 150° C., preferably from about 80° C. to about 100° C. for a time sufficient to complete the reaction. Then from about 0.5 to about 1.0 moles of this product can be reacted with the product of (1) under conditions specified under (2) above for the complexing reaction.

(6) The reaction of alkenylsuccinic anhydride, ester or acid with an alkyl phenyl ether The reaction conditions, proportions and the like stated for reaction (1) will apply.

The alkyl phenyl ethers (or, as they are sometimes called, phenol ethers), have the formula

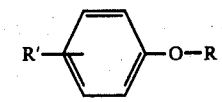

wherein R is a hydrocarbyl of from 1 to 18 carbon atoms, and R' is hydrogen or the same as R. When R and R' are hydrocarbyls, they may be the same or different. Preferably R is an alkyl of from 1 to 8 carbon atoms and R' is hydrogen.

Having described the invention in general terms, the following examples are offered as illustrations of the invention. Unless otherwise stated, "parts" are parts by weight.

EXAMPLE 1

Example 1 illustrates the basic reaction between an alkenylsuccinic anhydride and a phenolic material.

A reactor was charged with 3200 parts polybutenylsuccinic anhydride (prepared from 1300 molecular weight polybutene and maleic anhydride), 240 parts of a 1:2 molar boron trifluoride phenol complex and 4395 parts benzene solvent. The mixture was stirred for one hour at 85° C. and then stripped of solvent, catalyst and unreacted phenol by heating to 105° C. for 2 hours at 2 mm of Hg. Infrared analysis indicated that the product was a mixture but the main absorbtions were due to presence of ortho and para substituted aromatics, phenolic hydroxyl and anhydride moieties.

EXAMPLE 2

This Example illustrates the alkylation of phenol by an ester derivative of the succinic anhydride.

A mixture of 60 parts dibutyl ester of the polybutenylsuccinic anhydride used in Example 1, 4 parts BF-phenol complex containing $BF_3$ to phenol in a molar ratio of 1:2 and 88 parts benzene was allowed to react overnight. Catalyst and unreacted phenol were removed by washing with hot water until the pH of the final wash was 3-4. Residual volatile materials were removed by vacuum stripping. Infrared analysis showed strong phenolic hydroxyl and aliphatic ester bands.

EXAMPLE 3

The Example illustrates the reaction of phenyl ethers with alkenylsuccinic anhydride.

Boron tifluoride was bubbled into 10.8 parts anisole

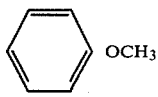

at room temperature until 6.7 parts by weight were absorbed. This solution was refluxed for four hours with 32 parts of polybutenylsuccinic anhydride (used in Example 1) and 57 parts benzene. The solvent, catalyst and unreacted anisole were then removed at 150° C. for 2 hours at 2 mm of mercury. The infrared curve showed strong absorption bands for anhydride, substituted aromatic and ether moieties.

EXAMPLE 4

A mixture of 138 parts polybutenylsuccinic anhydride, 7.6 parts resorcinol, 4.8 parts of 1:1 molar boron trifluoride-ethylether complex and 44 parts benzene were refluxed for 45 minutes. The mixture was further diluted with 123 parts benzene, washed three times with 120 ml portions of 17% aqueous isopropanol and stripped of volatiles at 150° C. for two hours at 1.5 mm of mercury. The infrared absorption curve showed a broad band at 1740 cm$^{-1}$ and a strong peak at 1705 cm$^{-1}$ indicating the presence of ester and acidic material as well as phenolic and anhydride components.

EXAMPLE 5

A refluxing solution of 4.1 parts resorcinol in 44 parts benzene was treated with a heated mixture of 70.4 parts polybutenyl succinic anhydride, 2.6 parts of 1:1 molar BF$_3$ ether complex and 88 parts benzene. The reaction was maintained at reflux for 10 minutes and quenched by pouring into an ice-water mixture. The product was worked up as in Example 4 and contained much less ester and acid than that example.

EXAMPLE 6

Twenty-two parts α-naphthol was dissolved in 200 parts benzene and 5.3 parts BF$_3$ was added. This solution was added to 367 parts of the PBSA used in Example 1 and the reaction mixture was refluxed for one hour before work-up by stripping at 175° C. for 2 hours at 2 mm of mercury. Ultraviolet absorption analysis confirmed the presence of naphthalene derivatives in the product and the expected absorptions were found in the infrared.

EXAMPLE 7

The product of Example 1 (2381 parts) was treated with tetraethylenepentamine (94.5 parts) at 150° C. for one hour and then held for two hours at this temperature under a 2 mm of mercury vacuum. The product, diluted with 819 parts Promor oil and filtered, was found to contain 0.73% nitrogen. Promor oil is a refinery process oil produced by the furfural extraction of a high paraffin feed stream. It has low aromatic and naphthenic contents and a very low percentage of sulfur. Its viscosity is such that the oil is suitable as a solvent in certain commercial operations.

EXAMPLE 8

A solution of zinc methanesulfonate was prepared from 7 parts zinc oxide, 22.6 parts of a 70% aqueous solution of methanesulfonic acid and 41.4 parts water. To this solution was added 15.5 parts tetraethylenepentamine over a one hour period. A solution of 375.5 parts Example 1 product in 176.7 parts Promor oil was added, and the materials were reacted at 150° C. for two hours under a vacuum of 2 mm of mercury. The product, after dilution with 160.7 parts Promor oil, and filtration, contained 0.40% nitrogen, 0.45% zinc and 0.36% sulfur.

EXAMPLE 9

Two hundred twenty parts polypropenylsuccinic anhydride (from 850 molecular weight polypropylene), 39 parts of a 1:2 BF$_3$-phenol complex and 228 parts benzene were refluxed 1.5 hours and then stripped of volatiles at 150° C. for two hours under 2 mm of mercury vacuum. Tetraethylenepentamine (23 parts) was added and the reactor was held under the same conditions for an additional 2 hours. The product was diluted with 93 parts of an ester made from a lower alkyl acid mixture and pentaerythritol and filtered. Infrared analysis confirmed the presence of phenol, amine and imide groups.

EXAMPLE 10

The product of Example 7 (247.7 parts) was treated with 2.3 parts paraformaldehyde added in portions over a 1.5 hour period at 80° C. The mass was heated at 100° C. for two hours and then stripped of volatiles at 150° C. for 3 hours at 2 mm of mercury before filtration. The infrared pattern showed distinct changes in both the aromatic substitution pattern and in the amine region. A control reaction between paraformaldehyde and a non-phenolated succinimide only showed changes in the amine region.

EXAMPLE 11

The product of Example 10 (100 parts was heated and stirred with 10.5 parts of a 38% aqueous solution of zinc methanesulfonate at 90° C. for one hour. After stripping the water from the mixture at 150° C. for 1 hour under 2 mm of mercury, the product was diluted with 38 parts Promor oil and filtered. The material contained 0.54% zinc, 0.69% nitrogen and 0.80% sulfur.

EXAMPLE 12

The product of Example 1 (505 parts) and 23 parts 2-amino-2(hydroxymethyl)-1,3-propanediol were reacted at 150° C. for 2 hours under 2 mm of mercury vacuum, diluted with 175 parts Promor oil and filtered. The product contained 0.38% nitrogen.

EXAMPLE 13

The product of Example 6 (255 parts) was diluted with 177 parts Promor oil and mixed with 11 parts tetraethylenepentamine. Reaction conditions were the same as for Example 8. The product contained 0.84% nitrogen.

EVALUATION OF PRODUCTS

The materials of Examples 7–12 were evaluated as detergent additives for lubricating oils in the Diesel Oil Test. The formulation used was comprised of 1.6% calcium sulfonate, 0.4% calcium phenate, 1% zinc isopropyl-ethylhexylphosphorodithioate and 2% (non-oil basis) experimental detergent in solvent-refined paraffinic neutral and bright oils blended to provide a 62–64 SUS viscosity grade. The base fluid and the same base fluid containing the aforementioned individual additives were next subjected for evaluation in a diesel oil test. This test was developed to produce deposits from the oxidation of lubricating oil under conditions which closely approximate those found in the piston zone of a diesel engine. The test consists of an aluminum cylinder heated by radiant energy from an internal heater. The surface temperature of the heater is maintained at 575° F. during the test period (140 minutes). The shaft turns slowly (2 RPM) and dips into an oil sump where it picks up a thin film of oil. This thin film is carried into the oxidation zone where heated gases (moist air at 350° F. is typically employed; however, nitrogen oxides, sulfur oxides and other mixtures can be used) form oxidation deposits. These deposits can be affected by the detergent as the test cylinder rotates into the sump. The efficiency of the detergent is rated by the color and intensity of the deposit on the shaft at the end of the test. The comparative results obtained, employing this test, are shown in the following table.

| Example | 140 Min. Rating | Control Rating |
| --- | --- | --- |
| 7 | 80 | 61 |
| 8 | 83 | 82 |
| 10 | 79 | 64 |
| 11 | 77 | — |
| 9 | 75 | — |

Products were also evaluated in a 1-G Caterpillar engine test. This test is performed to evaluate detergency characteristics of an additive. The formulation used was comprised of 1.6% calcium sulfonate, 0.4% calcium phenate, 1% zinc isopropylethylhexylphosphorodithioate and 2% (non-oil basis) experimental detergent in solvent-refined paraffinic neutral and bright oils blended to provide a 62–64 SUS viscosity grade. The engine is periodically dismantled and inspected for carbon and lacquer deposits with the following results after 120 hours of operation.

|  | Piston Rating | Lacquer Demerits | % Packing |
| --- | --- | --- | --- |
| Example 8 | 68.3 | 19.4 | 94 |
| Control | 47 | 37.4 | 51 |

These tests indicate the substantial improvements in lubricants which can be obtained by the use of the novel compositions of matter of this invention. In particular, the excellent dispersant properties of these products should be noted.

The additives of this invention can be used in any one of the wide variety of oils of lubricating viscosity, such as natural, refined or synthetic oils, in blends of such oils, or in greases made therefrom. These oils may be prepared with or without auxiliary conventional additives such as: oiliness and extreme pressure agents; corrosion, oxidation and rust inhibitors; viscosity index improving agents; coloring agents and auxiliary detergents. The useful oils include mineral oils, both naphthenic and paraffinic, either or both containing aromatic fractions. They include among the synthetic oils the synthetic hydrocarbon oils as well as synthetic ester oils prepared from, for example, monohydric alcohols and polyfunctional acids or from the polyhydric alcohols and monofunctional acids. In this latter category are esters prepared from pentaerythritol and a $C_5$ aliphatic mono acid such as valeric acid or from such alcohol and a mixture of $C_5$–$C_9$ aliphatic monofunctional acids.

The fuels contemplated are liquid hydrocarbon combustion fuels, including the distillate fuels, i.e. gasoline and fuel oils. Accordingly, the fuel oils that may be improved in accordance with the present invention are hydrocarbon fractions having an initial boiling point of at least about 100° F. and an end-boiling point no higher than about 750° F. and boiling substantially continuously throughout their distillation range. These fuel oils are generally known as distillate fuel oils. It is to be understood, however, that this term is not restricted to straight run distillate fractions. The distillate fuel oils can be straight run distillate fuel oils, catalytically or thermally cracked (including hydrocracked) distillate fuel oils, or mixtures of straight run distillate fuel oils, naphthas and the like, with cracked distillate stocks. Moreover, such fuel oils can be treated in accordance with well-known commercial methods, including acid or caustic treatment, hydrogenation, solvent refining, clay treatment and the like.

The distillate fuel oils are characterized by their relatively low viscosities, pour points, and similar properties. The principal property which characterizes the contemplated hydrocarbons, however, is the distillation range. As mentioned hereinbefore, this range lies between about 100° F. and about 750° F. Obviously, the distillation range of each individual fuel oil will cover a narrower boiling range, but falling, nevertheless, within the above-specified limits. Likewise, each fuel oil will boil substantially continuously throughout its distillation range.

Contemplated among the fuel oils are Nos. 1, 2 and 3 fuel oils (useful in heating and in diesel engines) and the jet combustion fuels. The domestic fuel oils generally conform to the specifications set forth in A.S.T.M. Specifications D396-48T. Specifications for diesel fuels are defined in A.S.T.M. Specification D975-48T. Typical jet fuels are defined in Military Specification MIL-F-5624B.

The gasolines that are improved by the additive compositions of this invention are mixtures of hydrocarbons having an initial boiling point falling between about 75° F. and about 135° F. and an end-boiling point falling between about 250° F. and about 450° F. As is well known in the art, motor gasoline can be straight run gasoline or, as is more usual, it can be a blend of two or more cuts of materials including straight run stock, catalytic or thermal reformate, cracked stock, alkylated natural gasoline and aromatic hydrocarbons. All of these are contemplated.

The invention has been described in terms of specific embodiments set forth in detail, but it should be understood that these are by way of illustration only and that the invention is not necessarily limited thereto. Alternative embodiments will become apparent to those skilled in the art in view of this disclosure, and accordingly, modifications of the product and process disclosed herein are to be contemplated within the spirit of this invention.

I claim:

1. A lubricant and fuel composition comprising a member selected from the group consisting of a lubricating oil, a grease thereof and a liquid hydrocarbon fuel and a detergent amount of the product of reaction between an alkenylsuccinic acid, anhydride or ester, wherein the alkenyl group is a $C_{25}$-$C_{300}$ unsaturated hydrocarbon, and a hydroxyaromatic compound and the alkyl-substituted members thereof, the reaction being run such that (1) there are from about 0.1 to about 10 moles of hydroxyaromatic compound per mole of the alkenylsuccinic compound, (2) the temperature is at from about $-20°$ C. to about 225° C. and (3) there is a catalyst present to direct the addition of the hydroxyaromatic compound to the alkenyl group of the succinic compound.

2. The composition of claim 1 wherein the hydroxyaromatic compound is phenol.

3. The composition of claim 1 wherein the hydroxyaromatic compound is naphthol.

4. The composition of claim 1 wherein the alkenylsuccinic compound is polybutenylsuccinic anhydride.

5. The composition of claim 4 wherein the polybutenyl has a molecular weight of 1300.

6. The composition of claim 1 wherein the alkenylsuccinic compound is polypropenylsuccinic anhydride.

7. The composition of claim 6 wherein the polypropenyl has a molecular weight of 850.

8. The composition of claim 1 wherein the alkenyl contains from 50 to about 300 carbon atoms.

9. The composition of claim 1 wherein the hydroxyaromatic compound reactant is in the form of a $BF_3$ complex thereof.

10. The composition of claim 1 wherein the lubricant is a lubricating oil.

11. The composition of claim 10 wherein the oil is a mineral oil.

12. The composition of claim 10 wherein the oil is a synthetic ester oil.

13. A lubricant and fuel composition comprising a member selected from the group consisting of a lubricating oil, a grease thereof and a liquid hydrocarbon fuel and a detergent amount of the product of reaction between the product as outlined in claim 1 and an amine selected from the group consisting of an amino alkanepolyol and a polyalkylenepolyamine, in which the reaction is run at from about 50° C. to about 250° C. and in which the reaction mixture contains from 0.1 to about 3.0 moles of amine per mole of said product defined in claim 1.

14. The composition of claim 13 wherein the polyalkylanepolyamine is tetraethylenepentamine.

15. The composition of claim 13 wherein the lubricant is a lubricating oil.

16. The composition of claim 15 wherein the oil is a mineral oil.

17. The composition of claim 15 wherein the oil is a synthetic ester oil.

18. A lubricant and fuel composition comprising a member selected from the group consisting of a lubricating oil, a grease thereof and a liquid hydrocarbon fuel and a detergent amount of the product of reaction between the product as outlined in claim 13 and an aldehyde, in which the reaction is run at from about 30° C. to about 200° C. and in which the reaction mixture contains from about 0.1 moles to about 5.0 moles of aldehyde per mole of said product defined in claim 13.

19. The composition of claim 18 wherein the aldehyde is paraformaldehyde.

20. The composition of claim 18 wherein the lubricant is a lubricating oil.

21. The composition of claim 20 wherein the oil is a mineral oil.

22. The composition of claim 20 wherein the oil is a synthetic ester oil.

23. A lubricant and fuel composition comprising a member selected from the group consisting of a lubricating oil, a grease thereof and a liquid hydrocarbon fuel and a detergent amount of the product of reaction between the product as outlined in claim 18 and from 0.1 to 3.0 moles per mole of said outlined product of a metal salt capable of complexing therewith, which metal ion is selected from Groups IB, IIB, VB, VIIB, VIII of the Periodic Table, tin and zirconium, the reaction being run at from about 50° C. to about 225° C.

24. The composition of claim 23 wherein the metal salt is zinc methanesulfonate.

25. The composition of claim 23 wherein the lubricant is a lubricating oil.

26. The composition of claim 25 wherein the oil is a mineral oil.

27. The composition of claim 25 wherein the oil is a synthetic ester oil.

28. A lubricant and fuel composition comprising a member selected from the group consisting of a lubricating oil, a grease thereof and a liquid hydrocarbon fuel and a detergent amount of the product of reaction between an alkenylsuccinic acid, ester or anhydride, wherein the alkenyl group is a $C_{25}$-$C_{300}$ unsaturated hydrocarbon, and an alkyl phenyl ether, the reaction being run such that (1) there are from about 0.1 to about 10 moles of the alkyl phenyl ether per mole of the alkenylsuccinic compound (2) the temperature is at from about $-20°$ C. to about 225° C. and (3) there is a catalyst present to direct the addition of the alkyl phenyl ether to the alkenyl group of the succinic compound.

29. The composition of claim 28 wherein the alkyl phenyl ether is anisole.

30. The composition of claim 28 wherein the alkylphenyl ether is in the form of a $BF_3$ complex thereof.

31. The composition of claim 28 wherein the lubricant is a lubricating oil.

32. The composition of claim 31 wherein the oil is a mineral oil.

33. The composition of claim 31 wherein the oil is a synthetic ester oil.

34. A lubricant and fuel composition comprising a member selected from the group consisting of a lubricating oil, a grease thereof and a liquid hydrocarbon fuel and a detergent amount of the product of reaction between the product as outlined in claim 13 and from about 0.1 to about 3.0 moles per mole of said outlined product of a metal salt capable of complexing therewith, which metal is selected from Groups IB, IIB, VB, VIIB, VIII of the Periodic Table, tin and zirconium, the reaction being run at from about 50° C. to about 150° C.

35. The composition of claim 34 wherein the amine is tetraethylene.

36. The composition of claim 34 wherein the hydroxyaromatic compound is phenol.

37. The composition of claim 34 wherein the alkenylsuccinic compound is polybutenylsuccinic anhydride.

38. The composition of claim 37 wherein the polybutenyl has a molecular weight of 1300.

39. The composition of claim 34 wherein the alkenyl contains from 50 to about 300 carbon atoms.

40. The composition of claim 34 wherein the metal salt is zinc methanesulfonate.

41. The composition of claim 34 wherein the lubricant is a lubricating oil.

42. The composition of claim 41 wherein the oil is a mineral oil.

43. The composition of claim 41 wherein the oil is a synthetic ester oil.

* * * * *

UNITED STATES PATENT AND TRADEMARK OFFICE
CERTIFICATE OF CORRECTION

PATENT NO. : 4,219,431
DATED : August 26, 1980
INVENTOR(S) : SHELDON CHIBNIK

It is certified that error appears in the above-identified patent and that said Letters Patent are hereby corrected as shown below:

Column 11, lines 44-45, "defined" should be --outlined--;

Column 11, lines 46-47, "polyalkylanepolyamine" should be --polyalkylenepolyamine--;

Column 11, line 62, "defined" should be --outlined--;

Column 12, line 53, "tetraethylene" should be --tetraethylenepentamine--.

Signed and Sealed this

Thirteenth Day of January 1981

[SEAL]

Attest:

SIDNEY A. DIAMOND

Attesting Officer     Commissioner of Patents and Trademarks